(12) United States Patent
Gottlieb et al.

(10) Patent No.: US 12,635,916 B2
(45) Date of Patent: May 26, 2026

(54) METHOD AND/OR SYSTEM FOR DETERMINING BLOOD GLUCOSE REFERENCE SAMPLE TIMES

(71) Applicant: Medtronic MiniMed, Inc., Northridge, CA (US)

(72) Inventors: Rebecca K. Gottlieb, Culver City, CA (US); Meena Ramachandran, San Francisco, CA (US)

(73) Assignee: Medtronic MiniMed, Inc., Northridge (CA)

( * ) Notice: Subject to any disclaimer, the term of this patent is extended or adjusted under 35 U.S.C. 154(b) by 6 days.

(21) Appl. No.: 18/588,645

(22) Filed: Feb. 27, 2024

(65) Prior Publication Data

US 2024/0197212 A1 Jun. 20, 2024

Related U.S. Application Data

(63) Continuation of application No. 17/552,264, filed on Dec. 15, 2021, now Pat. No. 11,957,459, which is a
(Continued)

(51) Int. Cl.
*A61B 5/145* (2006.01)
*A61B 5/00* (2006.01)
(Continued)

(52) U.S. Cl.
CPC ...... *A61B 5/14532* (2013.01); *A61B 5/14503* (2013.01); *A61B 5/4839* (2013.01); *A61B 5/6849* (2013.01); *A61B 5/7221* (2013.01);

*A61B 5/742* (2013.01); *A61M 5/14244* (2013.01); *A61M 5/1723* (2013.01);
(Continued)

(58) Field of Classification Search
None
See application file for complete search history.

(56) References Cited

U.S. PATENT DOCUMENTS 5,126,952 A 6/1992 Kildal-Brandt et al.
5,822,715 A 10/1998 Worthington et al.
(Continued)

FOREIGN PATENT DOCUMENTS

CN 102970927 B 12/2016
CN 107095681 A 8/2017
(Continued)

OTHER PUBLICATIONS

Bagshaw, S.M., et al., "The impact of early hypoglycemia and blood glucose variability on outcome in critical illness", Critical care medicine, 2009, vol. 13, No. 3, pp. 91.
(Continued)

*Primary Examiner* — Michael R Bloch
(74) *Attorney, Agent, or Firm* — Weaver Austin Villeneuve & Sampson LLP

(57) ABSTRACT

Techniques disclose herein relate to determining glucose reference sample times. The techniques may involve determining a first glucose reference sample measurement for a patient. The techniques may further involve determining timing information for obtaining a second glucose reference sample measurement based at least in part on readings from a continuous glucose sensor.

20 Claims, 13 Drawing Sheets

Related U.S. Application Data continuation of application No. 16/559,416, filed on Sep. 3, 2019, now Pat. No. 11,224,362, which is a continuation of application No. 15/268,063, filed on Sep. 16, 2016, now Pat. No. 10,433,774, which is a continuation of application No. 13/171,244, filed on Jun. 28, 2011, now abandoned.

(60) Provisional application No. 61/407,888, filed on Oct. 28, 2010, provisional application No. 61/361,876, filed on Jul. 6, 2010.

(51) Int. Cl.
*A61M 5/142* (2006.01)
*A61M 5/172* (2006.01)

(52) U.S. Cl.
CPC ............. *A61M 2005/14208* (2013.01); *A61M 2205/18* (2013.01); *A61M 2205/50* (2013.01); *A61M 2230/201* (2013.01)

(56) References Cited

U.S. PATENT DOCUMENTS

| | | | |
|---|---|---|---|
| 6,280,381 | B1 | 8/2001 | Malin et al. |
| 7,695,677 | B2 | 4/2010 | Werner et al. |
| 7,833,157 | B2 | 11/2010 | Gottlieb et al. |
| 8,657,746 | B2 | 2/2014 | Roy |
| 8,919,180 | B2 | 12/2014 | Gottlieb et al. |
| 9,033,878 | B2 | 5/2015 | Liang et al. |
| 9,402,569 | B2 | 8/2016 | Liang et al. |
| 10,433,774 | B2 | 10/2019 | Gottlieb et al. |
| 11,224,362 | B2 | 1/2022 | Gottlieb et al. |
| 11,957,459 | B2 | 4/2024 | Gottlieb et al. |
| 2002/0035318 | A1 | 3/2002 | Mannheimer et al. |
| 2002/0106709 | A1 | 8/2002 | Potts et al. |
| 2002/0161288 | A1 | 10/2002 | Shin et al. |
| 2003/0050546 | A1 | 3/2003 | Desai et al. |
| 2003/0130616 | A1 | 7/2003 | Steil et al. |
| 2005/0038332 | A1* | 2/2005 | Saidara ................... G16H 40/67 |
| | | | 128/920 |
| 2006/0020190 | A1 | 1/2006 | Kamath et al. |
| 2007/0016381 | A1 | 1/2007 | Kamath et al. |
| 2008/0161664 | A1 | 7/2008 | Mastrototaro et al. |
| 2008/0249386 | A1 | 10/2008 | Besterman et al. |
| 2008/0288180 | A1 | 11/2008 | Hayter et al. |
| 2008/0300572 | A1 | 12/2008 | Rankers et al. |
| 2009/0036747 | A1 | 2/2009 | Hayter et al. |
| 2009/0054753 | A1 | 2/2009 | Robinson et al. |
| 2009/0055149 | A1 | 2/2009 | Hayter et al. |
| 2009/0156924 | A1* | 6/2009 | Shariati ................ A61B 5/6848 |
| | | | 600/365 |
| 2009/0192751 | A1* | 7/2009 | Kamath ............... A61B 5/0004 |
| | | | 73/1.02 |
| 2010/0045465 | A1 | 2/2010 | Brauker et al. |
| 2010/0081909 | A1 | 4/2010 | Budiman et al. |
| 2010/0162786 | A1 | 7/2010 | Keenan et al. |
| 2010/0168538 | A1 | 7/2010 | Keenan et al. |
| 2010/0234710 | A1 | 9/2010 | Budiman et al. |
| 2011/0184268 | A1 | 7/2011 | Taub |
| 2011/0184269 | A1 | 7/2011 | Sauter-Starace et al. |
| 2011/0313390 | A1 | 12/2011 | Roy et al. |
| 2011/0320166 | A1 | 12/2011 | Luo et al. |
| 2012/0006100 | A1 | 1/2012 | Gottlieb et al. |
| 2012/0108932 | A1 | 5/2012 | Roy |
| 2013/0144254 | A1 | 6/2013 | Amirouche et al. |
| 2016/0175520 | A1 | 6/2016 | Palerm et al. |
| 2017/0065212 | A1 | 3/2017 | Gottlieb et al. |
| 2019/0388014 | A1 | 12/2019 | Gottlieb et al. |
| 2022/0104734 | A1 | 4/2022 | Gottlieb et al. |

FOREIGN PATENT DOCUMENTS

| | | | |
|---|---|---|---|
| CN | 107095681 | B | 3/2020 |
| WO | 0074753 | A1 | 12/2000 |
| WO | 2006050032 | A2 | 5/2006 |
| WO | 2008151452 | A1 | 12/2008 |
| WO | 2012006208 | A2 | 1/2012 |

OTHER PUBLICATIONS

CN Application. No. 201180033381.1 115.P019PCTCN: First Office Action, Mar. 26, 2014, 12 pages.
CN Application. No. 201180033381.1 115.P019PCTCN: Second Office Action Oct. 21, 2014, 12 pages.
CN Office Action dated May 6, 2015, 16 pages, in application No. CN201180033381.8.
CN Office Action dated on Nov. 3, 2015, 9 pages in application No. CN201180033381.8.
Communication pursuant to Article 94(3) EPC dated on Nov. 5, 2013, 4 pages in EP11731222.3.
Communication pursuant to Rule 69 EPC dated on Oct. 4, 2016, 2 pages, in EP16153071.2.
Communication under Rule 71(3) EPC, Sep. 28, 2018, 53 pages in EP16153071.2.
EP Application. no 11731222.3-1660/115.P019PCTEP: First Office action, mailed Nov. 5, 2013, 5 pages.
EP Application. no. 11731222.3-1660/115.P019PCTEP: Second office action, mailed Aug. 4, 2014, 4 pages.
EP Application No. 16153071.2-1666 I 3037037: Extended Search Report, Aug. 26, 2016, 10 pages.
EP Extended Search report dated Jul. 30, 2019, in Application No. 19150324.
EP Extened Search report dated Aug. 26, 2016, in Application No. 16153071.
EP Office Action dated on Sep. 25, 2015, 4 pages in EP11731222.3.
EP Partial Search report dated May 6, 2016, in Application No. 16153071.
EPO, European Office Action, dated Jan. 4, 2015, European Patent ApplicationNo. 11731222.3-1660, 4 pages.
EPO Office Action dated on Apr. 1, 2015, 4 pages in EP11731222.3.
EPO Office Action dated on Aug. 4, 2014, 4 pages in PCT/US2011/042560.
EPO Office Action dated on Nov. 5, 2013, 5 pages in PCT/US2011/042560.
Examiner's Report dated on Apr. 10, 2017, 4 pages in CA2802271.
Examiner's Report dated on Feb. 28, 2018, 4 pages in CA2802271.
Goldberg, P.A., et al., "Clinical Results of an Updated Insulin Infusion Protocol in Critically Ill Patients", Diabetes Spectrum, 2005, vol. 18(3), pp. 188-191.
Goldberg, P.A., et al., "Implementation of a Safe and Effective Insulin Infusion Protocol in a Medical Intensive Care Unit", Diabetes Car, 2004, vol. 27(2), pp. 461-467.
Hermandides, J., et al., "Glucose variability is associated with intensive care unit mortality", Critical care medicine, 2010, vol. 38, pp. 838-842.
International Preliminary Report on Patentability dated Jan. 17, 2013 in Application No. PCT/US2011/042560.
International Search Report and Written Opinion dated Mar. 9, 2012 in PCT Application No. PCT/US2011/042560.
Krinsley, U.S., et al., "Glycemic variability: A strong independent predictor of mortality in critically ill patients", Critical care medicine, 2008, vol. 36, No. 11, pp. 3008-3013.
Partial Search Report dated on May 6, 2016, 7 pages in EP16153071.2.
Response, filed Jan. 18, 2016, to Office Action dated Nov. 3, 2015, Chinese Patent Application No. 201180033381.8, 9 pages.
SIPO, Fifth Office Action, dated May 5, 2016, Chinese Patent Application No. 201180033381.8, 9 pages.
SIPO First Office Action dated on Mar. 26, 2013, 12 pages in PCT/CN101065060.
SIPO Second Office Action dated on Oct. 21, 2014, 12 pages in PCT/CN101065060.
Summons to attend oral proceedings pursuant to Rule 115(1) EPC dated on Apr. 1, 2015, 7 pages in EP11731222.3.
U.S. Appl. No. 13/171,244 I: Non-Final Rejection, mailed Nov. 4, 2014, 18 pages.

(56)  References Cited

OTHER PUBLICATIONS

U.S. Final Office Action dated Feb. 21, 2019, in U.S. Appl. No. 15/268,063.

U.S. Final office Action dated May 18, 2016 in U.S. Appl. No. 13/171,244.

U.S. Final office Action dated May 19, 2015 in U.S. Appl. No. 13/171,244.

U.S. Non-Final Office Action dated Jun. 21, 2018, in U.S. Appl. No. 15/268,063.

U.S. Non-Final Office Action dated Nov. 4, 2014, in U.S. Appl. No. 13/171,244.

U.S. Non-Final Office Action dated Oct. 15, 2015, in U.S. Appl. No. 13/171,244.

U.S. Non-Final Office Action dated Sep. 1, 2023, in U.S. Appl. No. 17/552,264.

U.S. Notice of Allowance dated May 16, 2019 in U.S. Appl. No. 15/268,063.

U.S. Notice of Allowance dated Nov. 29, 2023 in U.S. Appl. No. 17/552,264.

U.S. Notice of Allowance dated Sep. 4, 2019 in U.S. Appl. No. 15/268,063.

U.S. Notice of Allowance dated Sep. 16, 2021, in U.S. Appl. No. 16/559,416.

Van Den Berghe, G., et al., "Intensive Insulin Therapy in Critically Ill Patients" The New England Journal of Medicine, Nov. 8, 2001, vol. 345(19), pp. 1359-1367.

* cited by examiner

METHOD AND/OR SYSTEM FOR DETERMINING BLOOD GLUCOSE REFERENCE SAMPLE TIMES

This application is a continuation of U.S. patent application Ser. No. 17/552,264, filed 15 Dec. 2021 and titled "METHOD AND/OR SYSTEM FOR DETERMINING BLOOD GLUCOSE REFERENCE SAMPLE TIMES," which is a continuation of U.S. patent application Ser. No. 16/559,416, filed 3 Sep. 2019 and titled "METHOD AND/OR SYSTEM FOR DETERMINING BLOOD GLUCOSE REFERENCE SAMPLE TIMES," which is a continuation of U.S. patent application Ser. No. 15/268,063, filed 16 Sep. 2016 and titled "METHOD AND/OR SYSTEM FOR DETERMINING BLOOD GLUCOSE REFERENCE SAMPLE TIMES," which is a continuation of U.S. patent application Ser. No. 13/171,244, filed 28 Jun. 2011 and titled "METHOD AND/OR SYSTEM FOR DETERMINING BLOOD GLUCOSE REFERENCE SAMPLE TIMES," which claims the benefit of U.S. Provisional Patent Application No. 61/407,888, filed 28 Oct. 2010 and titled "DETERMINATION AND APPLICATION OF GLUCOSE SENSOR RELIABILITY INDICATOR AND/OR METRIC" and U.S. Provisional Patent Application No. 61/361,876, filed 6 Jul. 2010 and titled "ADAPTIVE TIMER FOR BLOOD GLUCOSE MEASUREMENT", the entire content of each application is incorporated herein by reference.

BACKGROUND

1. Field

Subject matter disclosed herein relates to monitoring blood glucose levels in patients.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals or trauma patients. As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

External infusion pumps are typically to control a rate of insulin infusion based, at least in part, on blood glucose measurements obtained from metered blood glucose samples (e.g., finger stick samples) or from processing signals received from a blood glucose sensor attached to a patient to provide sensor glucose measurements. By processing signals from such a blood glucose sensor, a patient's blood glucose level may be continuously monitored to reduce a frequency of obtaining metered blood glucose sample measurements from finger sticks and the like. However, measurements of blood glucose concentration obtained from processing signals from blood glucose sensors may not be as accurate or reliable as metered blood glucose sample measurements obtained from finger stick samples. Also, parameters used for processing blood glucose sensors for obtaining blood glucose measurements may be calibrated from time to time using metered blood glucose sample measurements as reference measurements obtained from finger sticks and the like. Accordingly, techniques for sensor-based continuous blood glucose monitoring typically still incorporate metered blood glucose sample measurements obtained from finger sticks and the like.

The so-called Yale Protocol provides one technique for determining a frequency for determining insulin infusion rates and time intervals between metered blood glucose sample measurements for insulin infusion therapy for a wide range of patients. Examples of the Yale Protocol may be found in Goldberg P A, Siegel M D, Sherwin, R S, et al. "Implementation of a Safe and Effective Insulin Infusion Protocol in a Medical Intensive Care Unit", Diabetes Care 27(2):461-467, 2004, and Goldberg P A, Roussel M G, Inzucchi S E. "Clinical Results of an Updated Insulin Infusion Protocol in Critically Ill Patients", Diabetes Spectrum 18(3):188-191, 2005. Regarding time intervals between metered blood glucose sample measurements, the Yale Protocol may specify a time between metered blood glucose sample measurements based on a currently observed blood glucose concentration and a rate of change at a last reference check.

SUMMARY

Techniques disclosed herein relate to determining glucose reference sample times. The techniques may be practiced with a processor-implemented method, a system comprising one or more processors and one or more processor-readable media, and/or one or more non-transitory processor-readable media.

In some embodiments, the techniques may involve determining a first glucose reference sample measurement for a patient. The techniques may further involve determining timing information for obtaining a second glucose reference sample measurement based at least in part on readings from a continuous glucose sensor.

BRIEF DESCRIPTION OF THE FIGURES

Non-limiting and non-exhaustive features will be described with reference to the following figures, wherein like reference numerals refer to like parts throughout the various figures.

DETAILED DESCRIPTION

Figure 1:
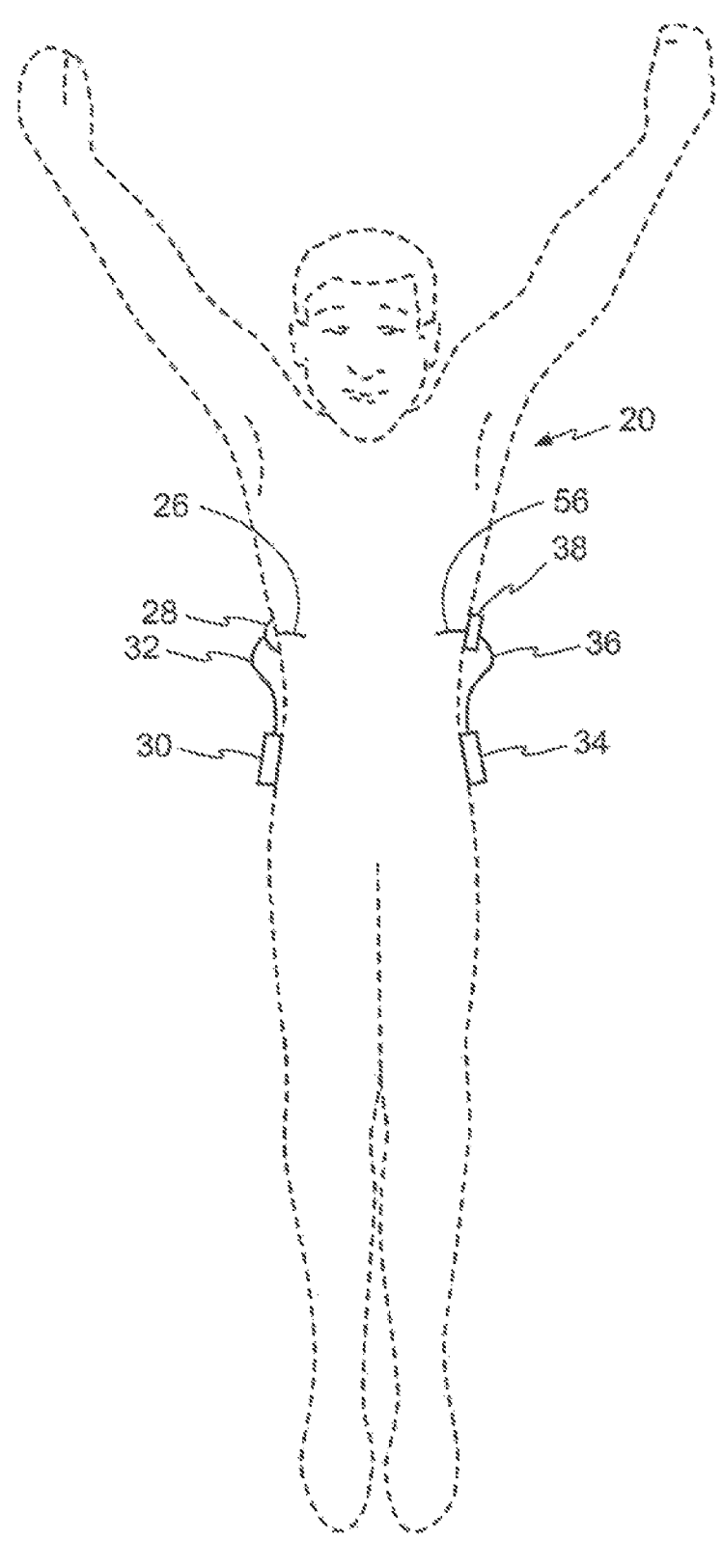
FIG. 1 is a front view of example devices located on a body in accordance with an embodiment.

In an example glucose control system environment, blood-glucose measurements may be obtained from a blood glucose sensor in any one of several different specific applications such as, for example, aiding in the application of insulin therapies in a hospital environment, controlling infusion of insulin in a patient-operated insulin infusion systems, just to name a few examples. In particular applications, a blood glucose sensor may be employed as part of a system to control infusion of insulin so as to control/maintain a patient's blood glucose within a target range, thus reducing a risk that the patient's blood glucose level transitions to dangerous extreme levels in the absence of action from the patient or treating attendant.

According to certain embodiments, example systems as described herein may be implemented in a hospital environment to monitor or control levels of glucose in a patient. Here, as part of a hospital or other medical facility procedure, a caretaker or attendant may be tasked with interacting with a patient's glycemic management system to, for example: enter blood-glucose reference measurements into control equipment to calibrate blood glucose measurements obtained from glucose sensors, make manual adjustments to devices, and/or make changes to therapies, just to name a few examples. Alternatively, a patient or other non-medical professional may be responsible for interacting with a closed-loop system to, for example, provide updated measurements of blood-glucose concentration obtained from metered blood glucose sample measurements or the like.

In addition to diet and amounts of insulin taken, other factors may affect a patient's blood glucose level such as, for example, exercise, stress, whether the patient is diabetic or recovering from surgery, just to provide a few examples. Receiving too little insulin or underestimating the carbohydrate content of a patient's meal may lead to prolonged hyperglycemia. Likewise, receiving too much insulin (e.g., by over-bolusing) for a given blood glucose level and/or meal may lead to hypoglycemia.

In particular applications, controlling acute hyperglycemia of critically ill patients is a high priority in ICU patient management. Particular treatment protocols may dictate closely managing patients' glucose levels by frequently checking glucose levels (e.g., using metered blood glucose sample measurements) according to a pre-determined and fixed schedule, ordered by a physician. This pre-determined and fixed schedule for glucose checks may not bring about cost effective patient management, as patients' glucose levels are measured per routine procedure instead of as appropriate according to the particular state of the patient. Given the dynamic nature of a critically ill patient's glucose levels, it may be beneficial to tailor a frequency of blood glucose measurements to an individual patient's state—dictating more frequent checks while the patient's glucose is labile, and dictating less frequent checks while the patient's glucose is relatively stable. This may not only improve patient care and outcomes, but may also more efficiently utilize clinical staff's time and resources.

To address issues associated with a fixed glucose check schedule, particular embodiments are directed to a dynamic, patient responsive glucose check timing process. In a particular implementation, continuous glucose monitoring may track patients' glucose levels on a minute-to-minute basis. Depending on a particular patient status defined by variables such as, for example, present sensor glucose level, sensor glucose rate of change, sensor glucose rate of increase or rate of decrease, sensor glucose 15-minute predicted value, sensor glucose reliability, and history of blood glucose reference checks, a time until a subsequent blood glucose reference sample may be determined.

Additionally, as a metered blood glucose sample measurement is received, a patient's attributes or status may be used to determine appropriate times to schedule a subsequent metered blood glucose sample measurement. If a sudden change has been made to a patient's therapy, including changes to nutritional intake status or medications, for example, the patient may be more susceptible to glucose swings, suggesting more frequent blood glucose reference checks. With a priori knowledge of any impending therapy changes, glucose swings may be predicted and averted. If clinical staff provides information to an adaptive time, indicating that a patient's glucose would soon rise or fall, the timer could proactively adjust the recommended time to the next metered blood glucose sample measurement to avoid excursions.

As pointed out above, the Yale Protocol provides one technique for determining a frequency for determining time intervals between metered blood glucose sample measurements for use in insulin infusion therapy for a wide range of patients and conditions. Here, a generalized approach to determining time intervals between metered blood glucose sample measurements to be short enough for addressing most, if not all, patients under most, if not all conditions. However, for some patients under some particular conditions, short time intervals between samples conservatively determined according to the Yale Protocol may not be necessary to provide a safe and effective glycemic management, for example. Here, depending on a particular application, obtaining metered blood glucose sample measurements more frequently than necessary may incur unnecessary inconvenience or cost. In a hospital environment, for example, safely increasing a time interval between metered blood glucose sample measurements to be obtained by an attendant may reduce a number of daily rounds for treating a particular patient. According to an embodiment, a metered blood glucose sample measurement may be obtained from a patient in combination with a blood glucose level in the patient observed from a continuous glucose monitoring sensor. In a particular implementation, a metered blood glucose sample measurement may be taken as finger stick measurements, metered blood glucose samples, just to name a couple of examples. Sensor blood glucose measurements may be obtained from processing signals received from a blood glucose sensor attached to a patient. While metered blood glucose sample measurements may provide reliable and accurate measurements of a patient's blood glucose level, these measurements are taken at discrete points in time. On the other hand, use of a blood glucose sensor allows for a continuous monitoring of a patient's blood glucose level.

According to an embodiment, metered blood glucose sample measurements obtained by an operator or attendant at discrete points in time may be used in combination with continuous glucose monitoring. In one application, use of continuous glucose monitoring may allow for more effective management of a patient's glycemic state between metered blood glucose sample measurements. In a particular implementation, on receipt of a metered blood glucose sample measurement from a patient, a time for obtaining a subsequent metered blood glucose sample measurement from the patient may be based, at least in part, on a metric indicative of a reliability of a sensor being used for continuous glucose monitoring. In an alternative embodiment, a time for obtaining a subsequent metered blood glucose sample measurement may be based, at least in part, on whether the patient's current observed blood glucose level is within a target blood glucose range.

In a particular implementation, the Yale protocol may be modified to consider additional factors to more closely tailor determination of time intervals between metered blood glucose sample measurements for particular patients. By more closely tailoring these time intervals, a cost or inconvenience associated with a continuous blood glucose monitoring and related therapies may be reduced.

Further, in another particular application, as a patient recovers from critical illness and his glucose stabilizes, an adaptive timer may observe continuous glucose sensor trends and a history of metered blood glucose sample measurements such that less frequent sample measurements checks are dictated. The adaptive timer may automatically extend a duration until the next recommended metered blood glucose sample measurement, or it could prompt the clinical staff for their input before adjusting any timing recommendation. For example, if a patient's sensor glucose has stabilized within a pre-determined target range for a pre-defined time duration, the Adaptive Timer for Blood Glucose Measurement can alert the clinical staff.

In a particular implementation, based, at least in part, on a review of a patient's glycemic status, a recommendation of an extension of time to a subsequent metered blood glucose sample measurement may be provided to a clinician. This may enable tailored patient care and better use of clinical staff's time to address issues as dictated by actual patient condition.

Overview of Example Systems

Figures 2A, 2B:
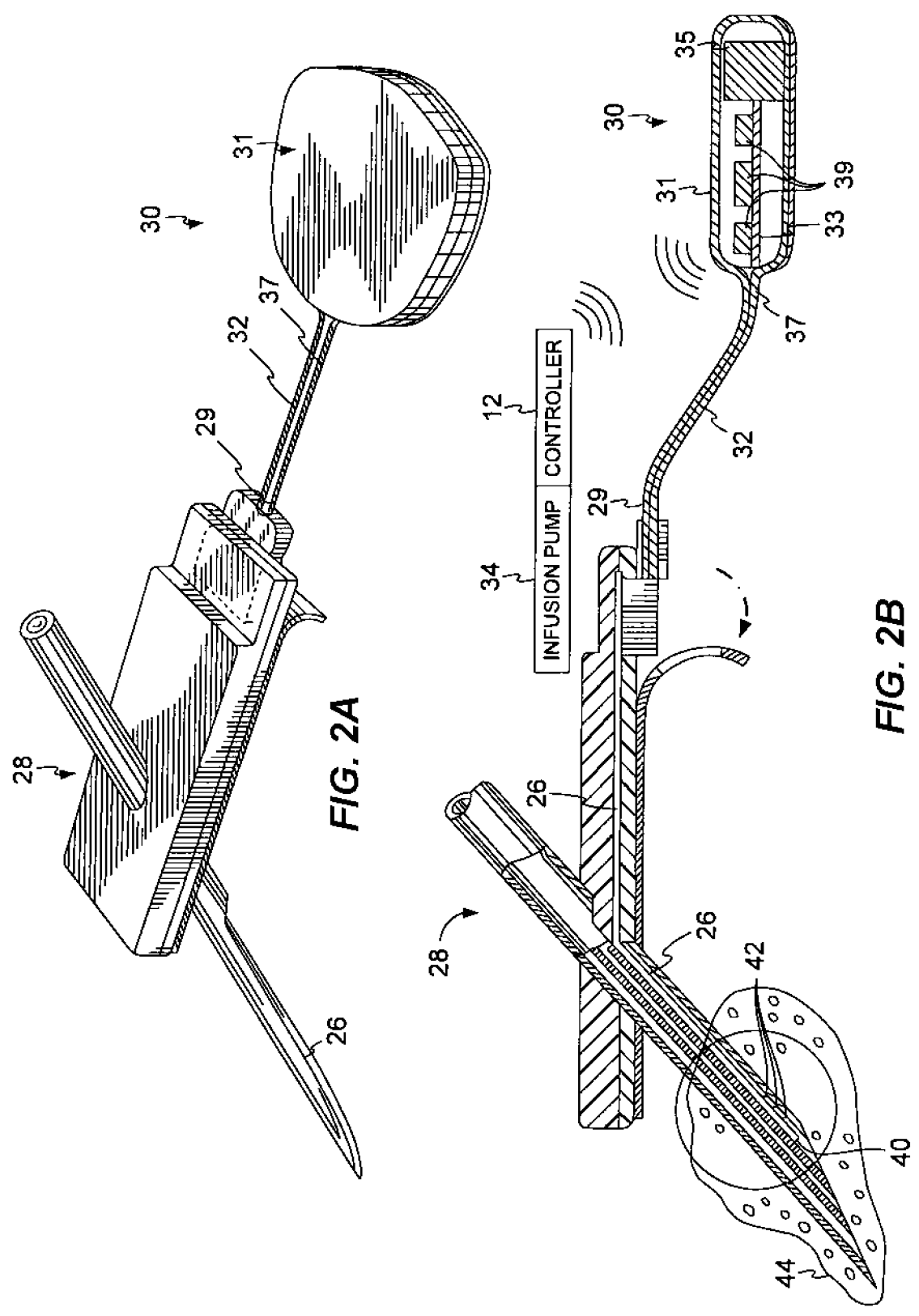
FIG. 2A is a perspective view of an example glucose sensor system for use in accordance with an embodiment.
FIG. 2B is a side cross-sectional view of a glucose sensor system of FIG. 2A for an embodiment.
Figure 2C:
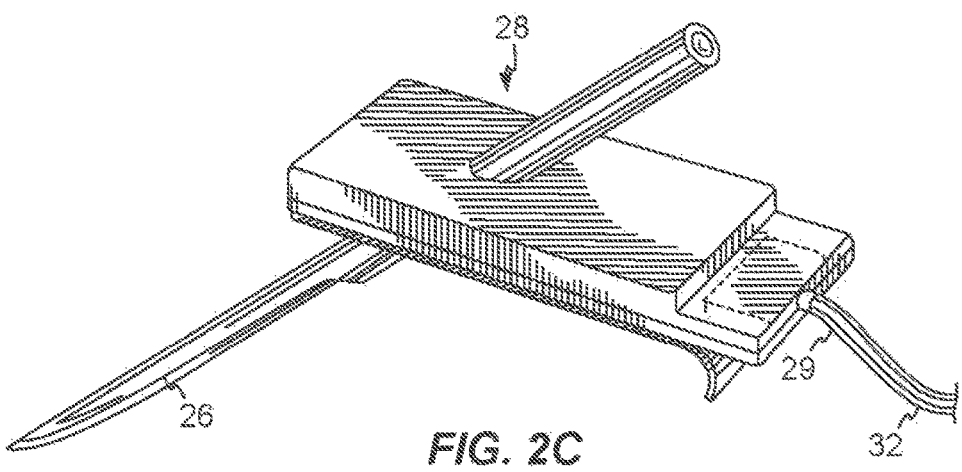
FIG. 2C is a perspective view of an example sensor set of a glucose sensor system of FIG. 2A for an embodiment.
Figure 2D:
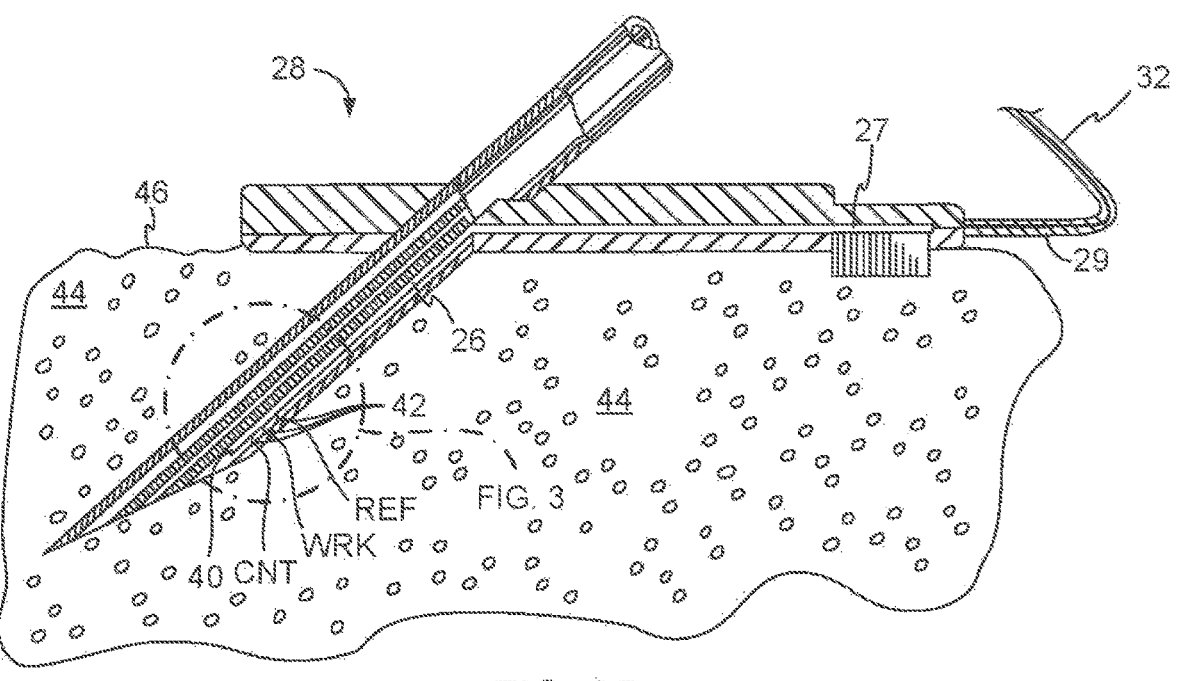
FIG. 2D is a side cross-sectional view of a sensor set of FIG. 2C for an embodiment.
Figure 3:
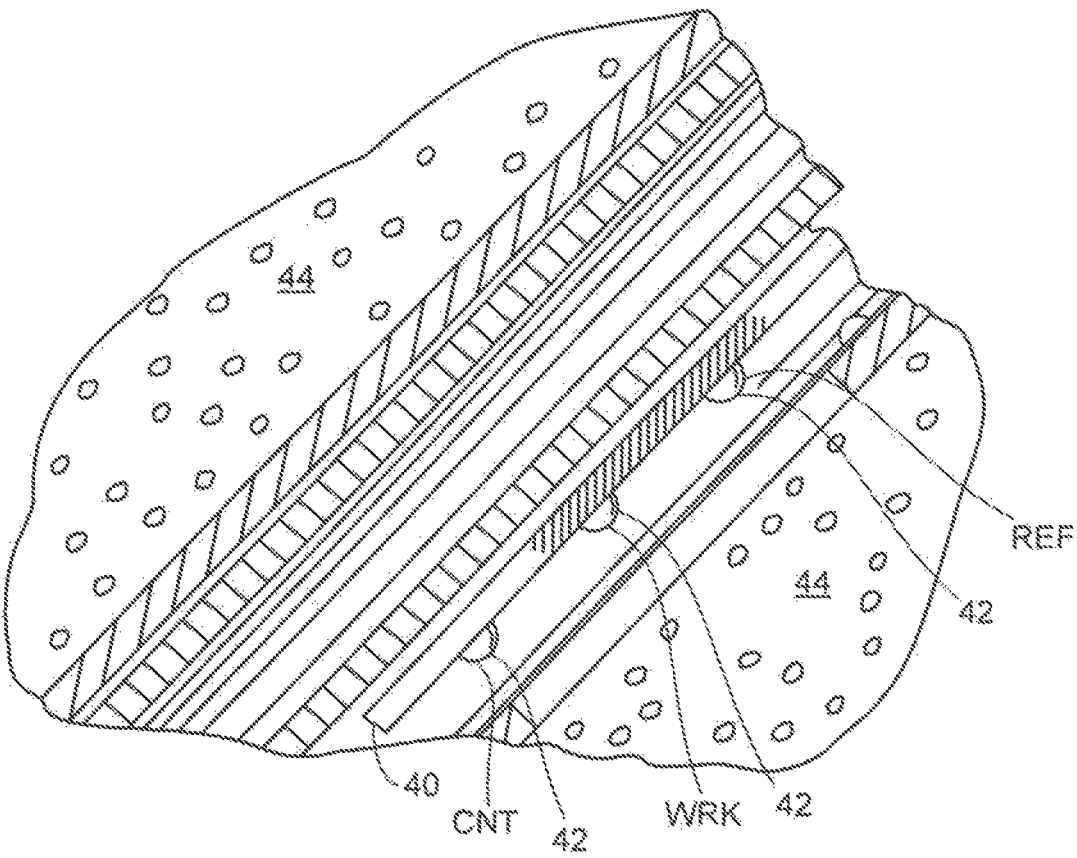
FIG. 3 is a cross sectional view of an example sensing end of a sensor set of FIG. 2D for an embodiment.
Figure 4:
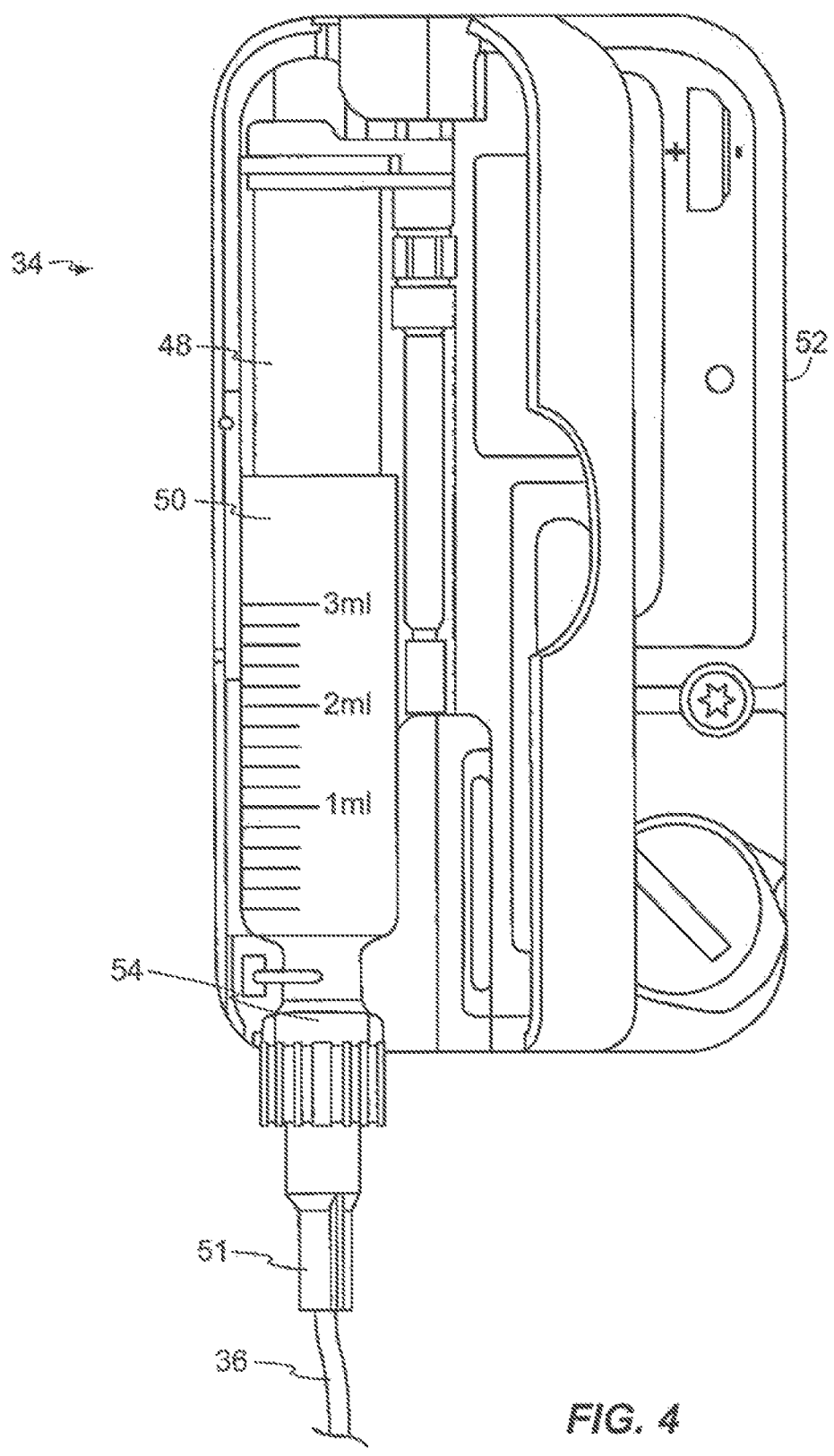
FIG. 4 is a top view of an example infusion device with a reservoir door in an open position, for use according to an embodiment.
Figure 5:
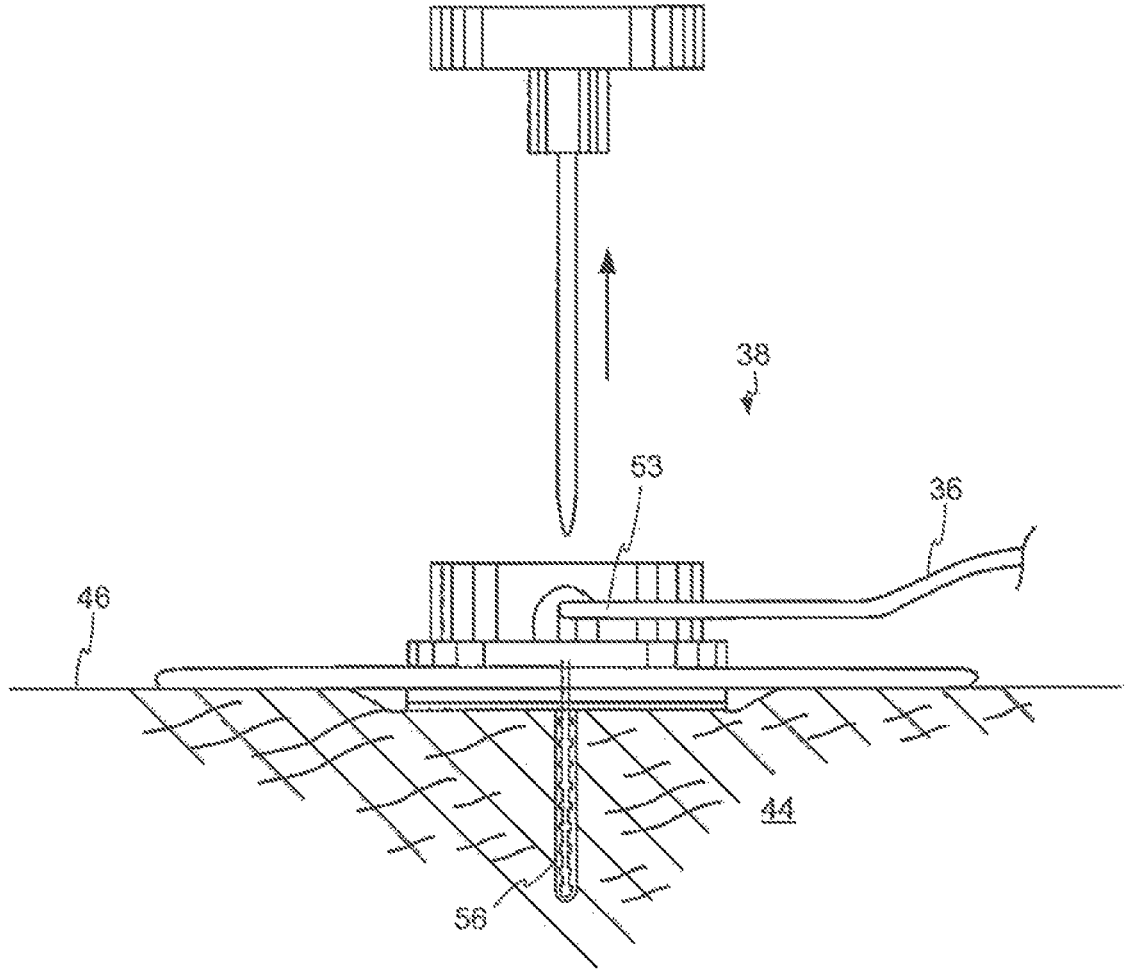
FIG. 5 is a side view of an example infusion set with an insertion needle pulled out, for use according to an embodiment.

FIGS. 1 through 5 illustrate example glucose control systems in accordance with certain embodiments. Such glucose control systems may be used, for example, in controlling a patient's glucose level about a target range as discussed above. It should be understood, however, that these are merely examples of particular systems that may be use for controlling a patient's glucose level about a target range and that claimed subject matter is not limited in this respect. FIG. 1 is a front view of example devices located on a body in accordance with certain embodiments. FIGS. 2A-2D and 3 show different views and portions of an example glucose sensor system for use in accordance with certain embodiments enabling continuous monitoring of a patient's blood glucose level. FIG. 4 is a top view of an example optional infusion device with a reservoir door in an open position in accordance with certain embodiments. FIG. 5 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 1. As shown in FIGS. 2A and 2B, telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 2D and 3. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 2C and 2D. Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample a sensor signal (not shown) and store digital sensor values (Dsig) in a memory. Digital sensor values Dsig may be periodically transmitted from a memory to a controller 12, which may be included in an infusion device.

With reference to FIGS. 1 and 4, a controller 12 may process digital sensor values Dsig and generate commands for infusion device 34. Infusion device 34 may respond to commands and actuate a plunger 48 that forces insulin out of a reservoir 50 that is located inside an infusion device 34. In an alternative implementation, glucose may also be infused from a reservoir responsive to commands using a similar and/or analogous device (not shown). In alternative implementations, glucose may be administered to a patient orally.

Also, controller 12 may collect and maintain a log or history of continuous measurements of a patient's blood glucose level to, for example, allow for characterization of a patient's glycemic trends. For example, and as illustrated below in particular example embodiments, a history of continuous blood glucose sensor measurements may enable prediction of a patient's blood glucose level at some time in the future.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 1 and 5). With reference to FIG. 5, insulin may be forced through infusion tube 36 into infusion set 38 and into a body of a patient. Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 4) and subcutaneous tissue 44 of a user's body 16.

As pointed out above, particular implementations may employ a closed-loop system as part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. The above described example components such as sensor 26, sensor set 28, telemetered characteristic monitor 30, sensor cable 32, infusion tube 36, infusion set 38, and so forth, are merely examples according to particular implementations and not intended to limit claimed subject matter. For example, blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to a patient. Other alternative embodiments may also include fewer, more, and/or different components than those that are described herein and/or illustrated in the accompanying Drawings.

As pointed out above, time interval between obtaining metered blood glucose sample measurements from a patient may be determined, at least in part, on whether the patient's blood glucose as observed from a blood glucose sensor signals is within a target range. In one particular implementation, a target range may be defined as a blood glucose concentration range where the patient's blood glucose level is at low risk of transitioning to dangerous extreme levels. For example, while a patient's blood glucose level is in such a target range, the risk of hypoglycemia and hyperglycemia to the patient may be low even if the patient, non-medical professional or medical professional is not obtaining frequent metered blood glucose sample measurements for effective glycemic management.

According to an embodiment, a target range may be defined, at least in part, by a target or set-point glucose level. Such a target or set-point glucose level may be based, at least in part, on a patient's particular physiology. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dl, which is in the normal glycemic range. Alternatively, target or set-point glucose level may be fixed at 120 mg/dl. In yet another alternative, a target or set-point blood glucose concentration may vary over time depending on particular patient conditions. It should be understood, however, that these are merely examples of a target or set-point blood glucose concentration, and claimed subject matter is not limited in this respect.

As pointed out above, an attendant or operator in a hospital environment may obtain metered blood glucose sample measurements from a patient according to a Yale protocol, for example. As discussed below with reference to specific examples illustrated in FIGS. 7 through 13, a time for obtaining a subsequent blood glucose reference sample may be lengthened under certain circumstances.

Figure 7:
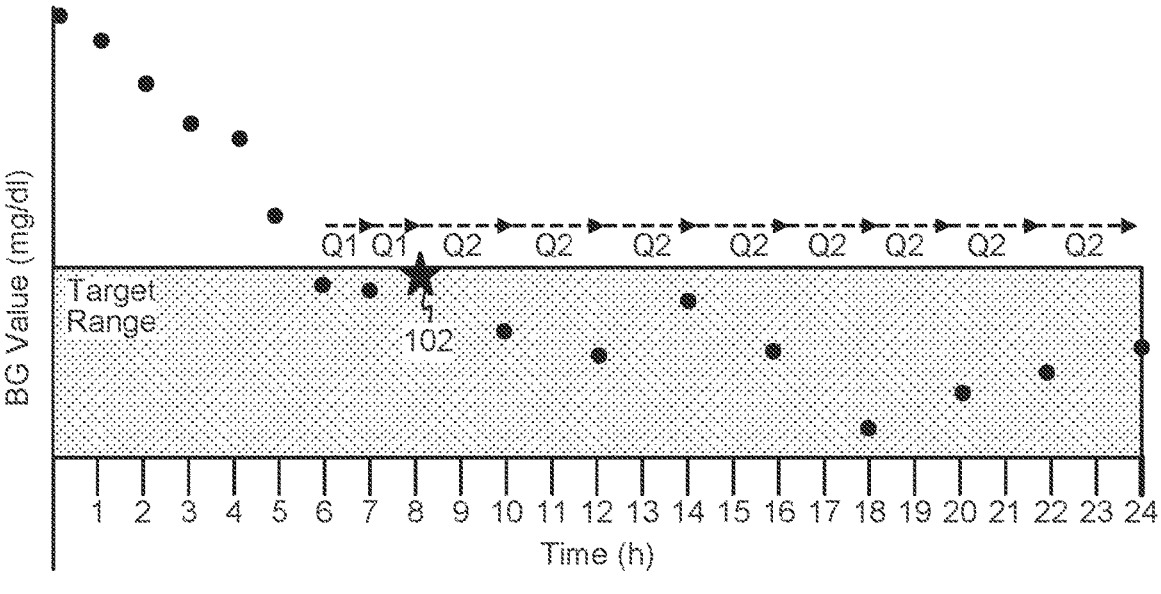
FIGS. 7 is a plot of metered blood glucose sample measurements taken of a patient at time intervals based, at least in part, on whether a patient's blood glucose level is observed to be within a target range, according to an embodiment.

FIGS. 7 through 16 are plots of a patient's blood-glucose level observed over a twenty-four hour period under different scenarios. A target range for a blood glucose level may be defined, for example, according to the patient's particular physiology as discussed above. FIG. 7 illustrates blood glucose levels as measured by metered blood glucose sample measurements such as finger stick sample measurements shown as plotted dots. Metered blood glucose sample measurements are taken on hourly intervals Q1 while the measured blood glucose level is above the target range, and then taken on two hour intervals Q2 following the third reference sample 102 in the target range (e.g., indicating that the patient's blood glucose level as stabilized). Intervals between metered blood glucose sample measurements may then remain at two hours while the measured blood glucose is within the target range.

In particular embodiments, as described herein with particular non-limiting examples, a time for obtaining a subsequent metered blood glucose sample measurement may be determined based, at least in part, on a "nearness" of a patient's observed blood glucose level (e.g., from continuous monitoring with a blood glucose sensor) to a target range. In one aspect, an observed blood glucose level to a target range may be determined based, at least in part, on whether a prediction of the observed blood glucose level is to be within the target range by a future time. In another alternative implementation, a nearness of an observed blood glucose level to the target range may be determined based, at least in part, on whether the observed blood glucose level is within the target range. In another alternative implementation, a nearness of an observed blood glucose level to a target range may be determined based, at least in part, on a difference between observed blood glucose level and an upper or lower bound of the target range. It should be understood, however, that these are merely examples of how a nearness of a patient's blood glucose level to a target range may be determined, and that claimed subject matter is not limited in this respect.

In a particular implementation, as an attendant or operator obtains a metered blood glucose sample from a patient (e.g., using a finger stick or other metered blood glucose measuring technique) the attendant or operator may input or provide a metered blood glucose sample value to a user interface of a controller (e.g., controller 12). The controller may then compute or determine a time for obtaining a subsequent metered blood glucose sample measurement based, at least in part, on one or more factors as discussed below. In alternative implementations, a controller may automatically receive a metered blood glucose sample measurement. As illustrated below in particular implementations, the controller may then indicate a time for obtaining a subsequent metered blood glucose sample measurement by, for example, displaying a time, sounding an alarm to let the operator or attendant know when to obtain the subsequent blood glucose reference sample, etc.

Figure 8:
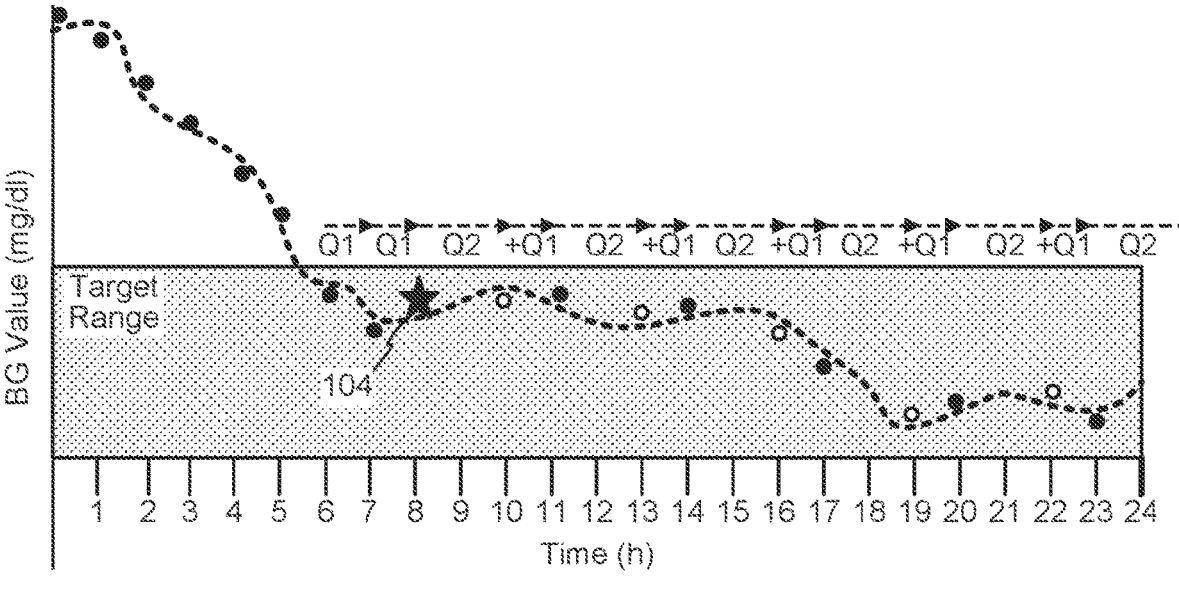
FIGS. 8 through 12 are plots illustrating an option to extend a time for obtaining a subsequent metered blood glucose sample measurement based, at least in part, on whether a patient's observed blood glucose level is within a target range, according to specific example embodiments.

In addition to using blood glucose reference samples for glycemic management, in the particular techniques illustrated in FIGS. 8 through 16 a controller may employ continuous glucose monitoring using a blood glucose sensor as discussed above. While a blood glucose level as observed from metered blood glucose sample measurements is shown as plotted dots, a blood glucose level as observed from continuous glucose monitoring using a blood glucose sensor is shown as a continuous dotted line. In FIG. 8, like the scenario of FIG. 7, a patient's blood glucose is measured with metered blood glucose samples on hourly intervals Q1 beginning while the observed blood glucose level is above the target range, and then measured on longer intervals following the third blood glucose sample measurement in the target range 104. However, with continuous glucose monitoring, a time for obtaining a subsequent metered blood glucose sample measurement may be extended safely beyond the two-hour intervals Q2 to Q2+Q1 (three hours) as shown. Here, responsive to receipt of a metered blood glucose sample measurement 104, a controller may give an attendant or operator an option to extend the time for obtaining a subsequent blood glucose reference sample by an additional hour. Here, the controller may display a message to the operator or attendant indicating the option to extend the time for obtaining the subsequent measurement. In the particular example shown, an 18% reduction in a total number of blood glucose reference samples over the particular example of FIG. 7 may be possible in the 24-hour period shown.

Figure 9:
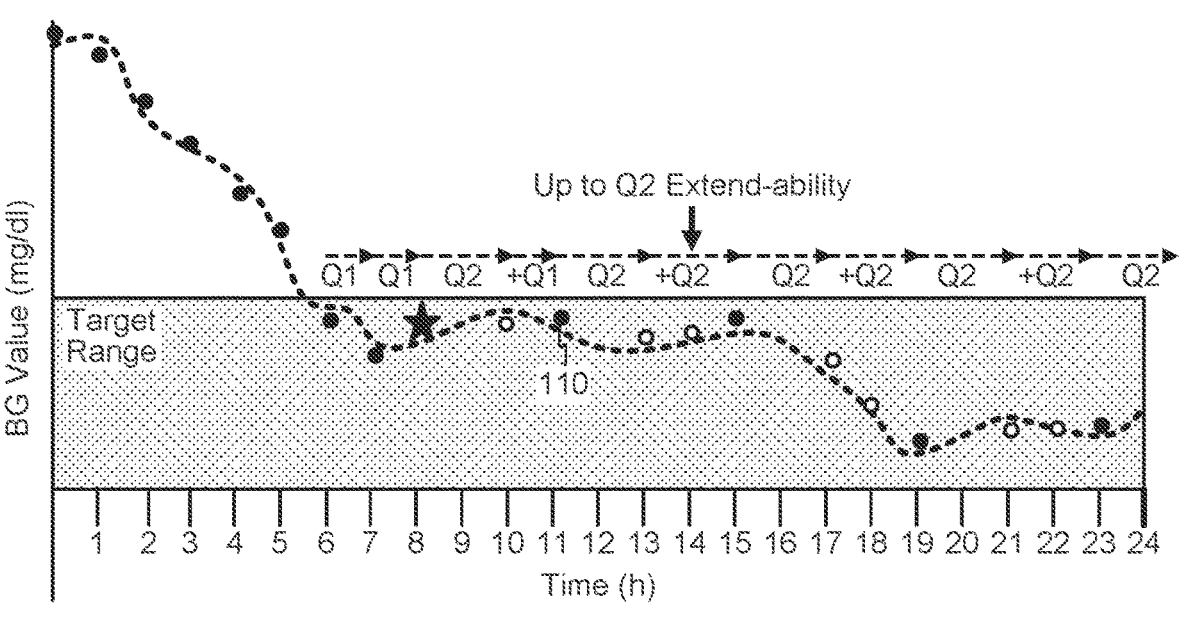

In FIG. 9 operation is similar to the scenario shown in FIG. 8 except that, in response to receipt of a fourth metered blood glucose sample measurement 110 (or over five hours within the target range), a controller may give an operator or attendant an option to extend a time for obtaining a subsequent metered blood glucose sample measurement from Q2+Q1 (or three hours) to Q2+Q2 (or four hours). This may allow for up to a 24% reduction in a total number of metered blood glucose sample measurements over the particular example of FIG. 7 in the 24-hour period shown.

Figure 10:
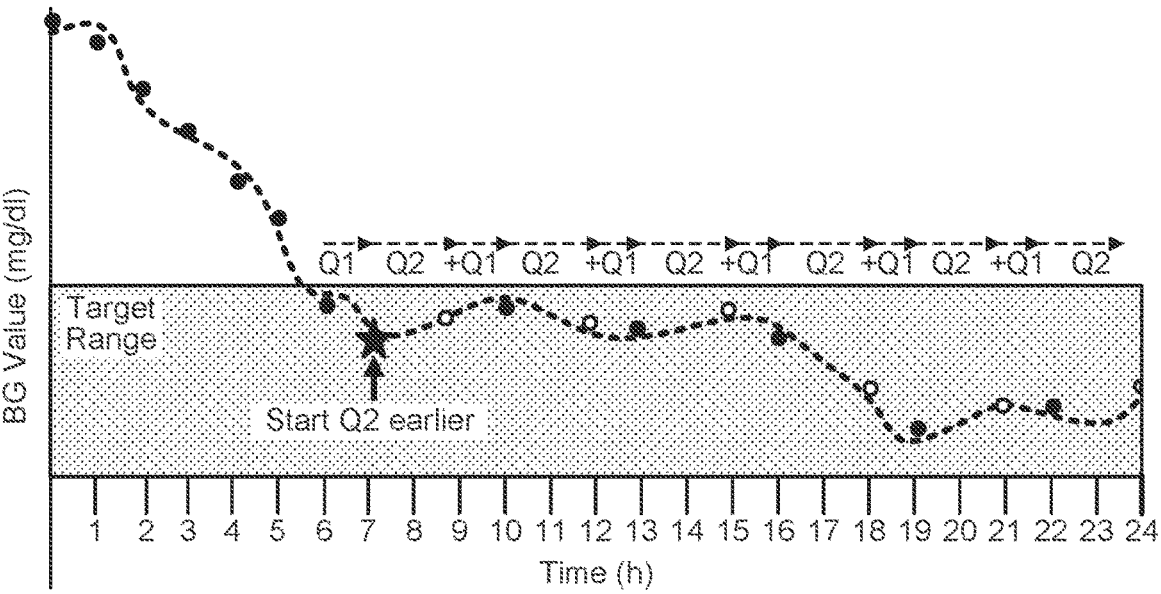

FIG. 10 illustrates operation which is similar to that of operation shown in FIG. 8 except that an operator or attendant is given an option to extend a time for obtaining a subsequent metered blood glucose sample measurement from Q2 (two hours) to Q2+Q1 (three hours) after the patient's blood glucose has been in a target range for only one hour. This may allow for up to a 24% reduction in a total number of blood glucose sample measurements over the particular example of FIG. 7 in the 24-hour period shown.

Figures 11, 12:
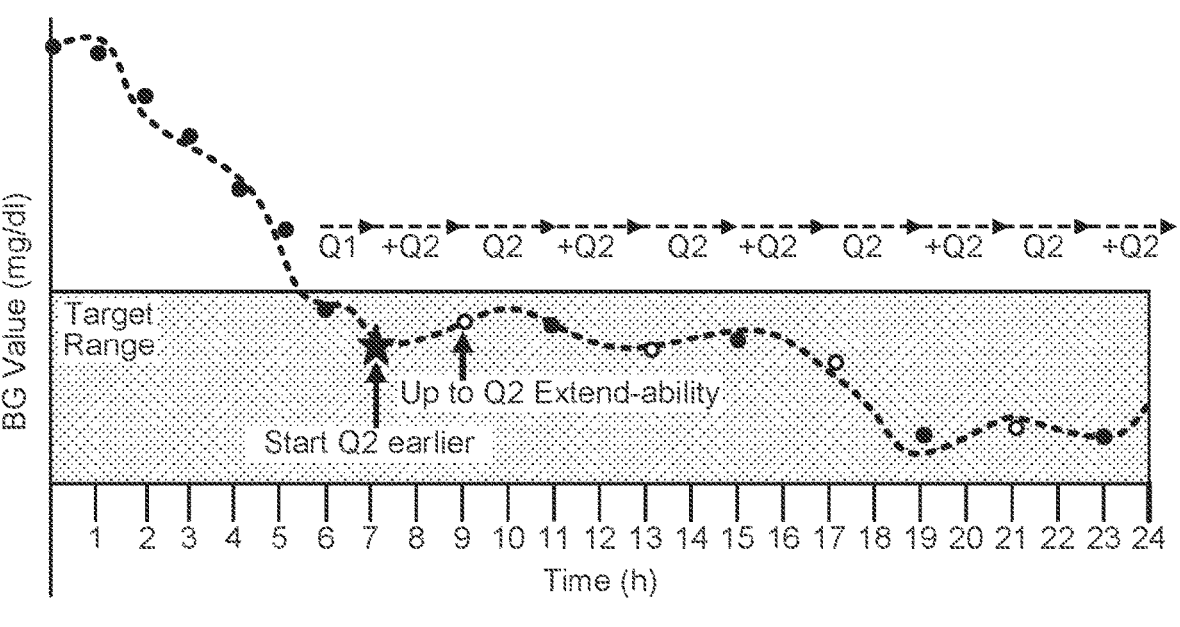

FIG. 11 illustrates operation which is similar to that of operation shown in FIG. 10, except that an operator or attendant is given an option to extend a time for obtaining a subsequent metered blood glucose sample measurement from Q2 (two hours) to Q2+Q2 (four hours) after the patient's blood glucose has been in a target range for one hour. This may allow for up to a 29% reduction in a total number of metered blood glucose sample measurements over the particular example of FIG. 7 in the 24-hour period shown.

FIG. 12 illustrates operation which is similar to that of operation shown in FIG. 11, except that an operator or attendant is given an option to extend a time for obtaining a subsequent metered blood glucose sample measurement from Q2 (two hours) to Q2+Q2 (four hours) immediately after as the patient's blood glucose has reached a target range (instead of after being in the target range for one hour). This may allow for up to a 35% reduction in a total number of blood glucose sample measurements over the particular example of FIG. 7 in the 24-hour period shown.

As illustrated above by example, a controller may allow an attendant or operator to optionally extend a time for obtaining a subsequent blood glucose reference sample under certain conditions. In these particular examples, such conditions may include 1) that a sensor glucose measurement indicates that a patient's blood glucose level is observed to be within a target range and 2) a length of time that the patient's sensor glucose measurement has been observed to be in the target range. In these particular implementations, accuracy or reliability of a blood glucose sensor may also be also be used for determining whether an attendant or operator may optionally extend a time for obtaining a subsequent metered blood glucose sample measurement. In a particular implementation, an additional condition for optionally extending a time for obtaining a subsequent metered blood glucose sample measurement may include a reliability indicator (RI), which may be expressed as a numerical value. Thus, conditions for optionally extending a time for obtaining a subsequent metered blood glucose sample measurement may be expressed as follows:

1. Sensor blood glucose (SBG) level observed to be within patient's target range;
2. SBG observed to be in patient's target range for more than a threshold duration; and
3. a reliability indicator (RI) comprising a numerical value expressing an indication of reliability of the blood glucose sensor exceeds a threshold value.

In a particular implementation, a controller may impose any or all of the above identified conditions for determining whether an attendant or operator may optionally extend a time for obtaining a subsequent metered blood glucose sample measurement. In a particular implementation, an RI numerically expressing a reliability of a glucose sensor may be computed using one or more techniques including, for example, analysis of observed trends in signals generated by the glucose sensor. Such observed trends may include, for example and without limitation, a reduced sensitivity of the glucose sensor, observed non-physiological anomalies or sensor drift as described in U.S. Provisional Application No. 61/407,888, filed on Oct. 28, 2010, which is herein incorporated by reference in its entirety. It should be understood, however, that these are merely examples of how a reliability indicator (indicative of a reliability of a blood glucose sensor) may be computed or derived for the purpose of determining a time for obtaining a subsequent metered blood glucose sample, and that other indicators of reliability may be used.

In one aspect, a presence of a patient's SBG in a target range or duration that the patient's SBG is in the target range may be an indicator of a stability of the patient's blood glucose level. In another aspect, a size of the target range in combination with a duration that the patient's SBG is in the target range may be an indicator of stability of the patient's blood glucose level. It should be understood, however, that these are merely examples of indicators of stability of a patient's blood glucose level which may be used in determining a time for obtaining a subsequent metered blood glucose sample, and that other indicators of stability may be used.

Figure 13:
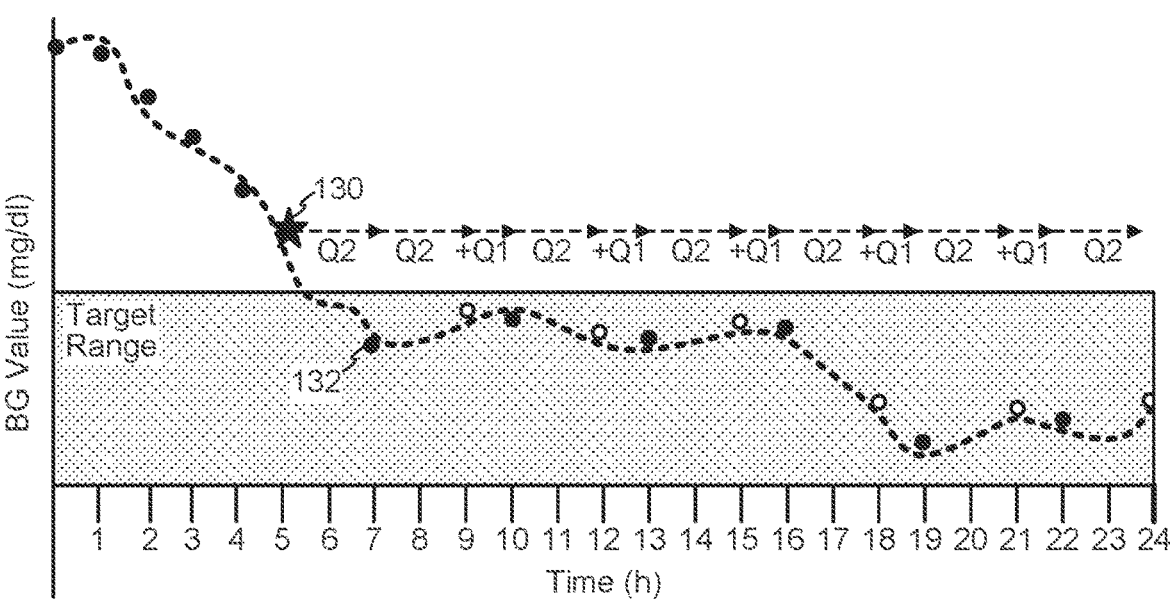
FIGS. 13 through 15 are plots illustrating an option to extend a time for obtaining a subsequent metered blood glucose sample measurement based, at least in part, on a patient's predicted blood glucose level, according to specific example embodiments.
Figure 14:
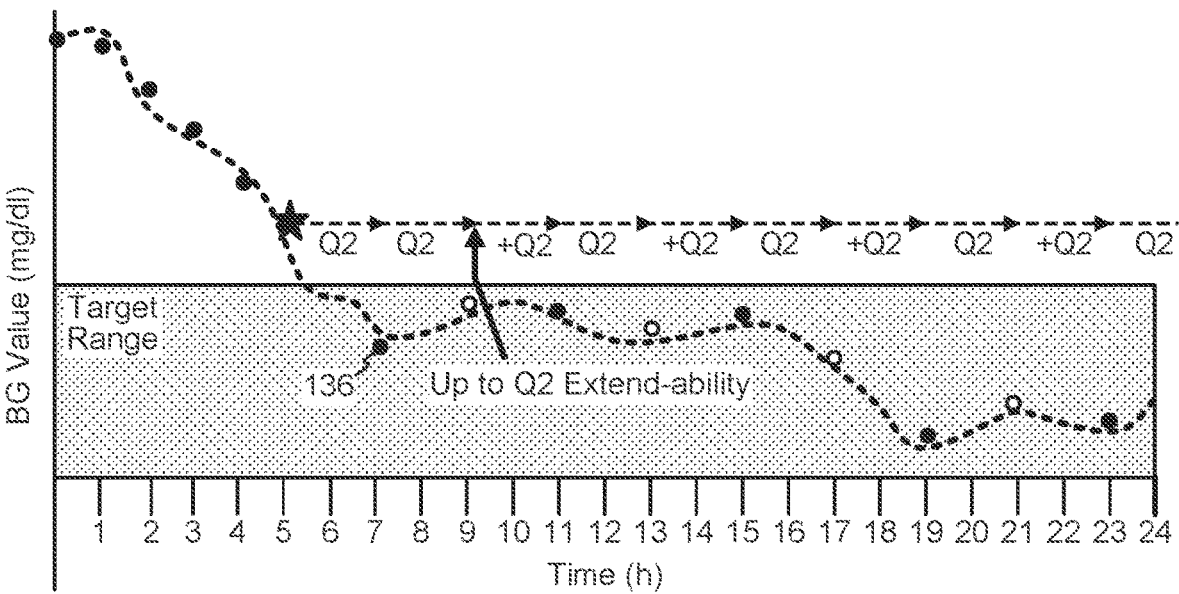
Figure 15:
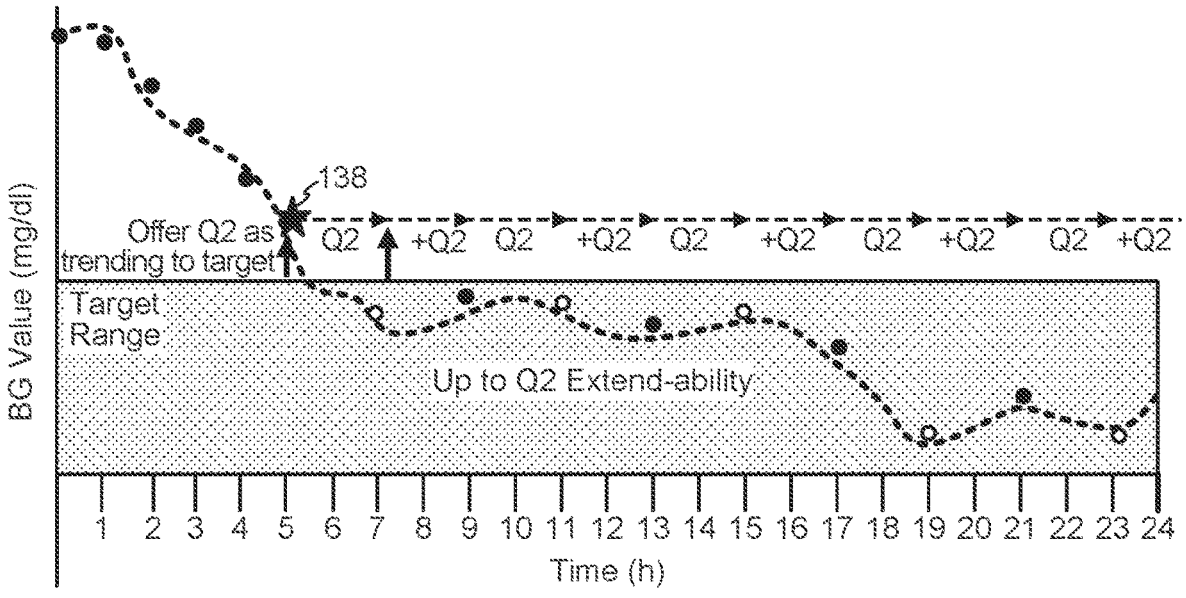

The particular examples illustrated in FIGS. 8 through 12 are directed to providing an operator or attendant with an option for extending a time for obtaining subsequent metered blood glucose sample measurement from a patient under certain conditions as discussed above (e.g., including whether blood glucose sensor measurements indicate that the patient's blood glucose level is in a target range). In these particular example implementations, a controller may give an operator or attendant the option to extend a time for obtaining a subsequent metered blood glucose sample measurement if a patient's sensor blood glucose is observed to be in a target range. FIGS. 13 through 15 are directed to an alternative implementation in which a time for obtaining a subsequent metered blood glucose sample measurement may be extended if a patient's sensor blood glucose is observed to be trending toward a target range but prior to reaching the target range. In one example implementation, if upon receipt of a metered blood glucose sample measurement a blood glucose level is predicted to be within a target range for a scheduled subsequent measurement sample time, the subsequent sample time may be extended. Such a prediction of a patient's blood glucose level may be based, at least in part, on a currently observed sensor blood glucose level in combination with an approximated first derivative of the sensor blood glucose level with respect to time. Furthermore, it is pointed out that change in a blood glucose level as observed though continuous glucose monitoring over time may be reflected in a non-stationary time series signal with trend and seasonality. Here, signals representing an observed blood glucose level may be non-stationary because of the statistical nature of sensor signals may change at least in part due to physiological change and many other factors. A trend in signals representing an observed blood glucose level may be at least partially affected by glucose control and/or patient recovery. A seasonality in signals representing an observed blood glucose level may be affected, at least in part, by a daily cycle of a patient's physiology. As such, any one of several time series forecasting and predicting techniques may be implemented for predicting a patient's blood glucose. Examples of techniques which may be applied to blood glucose sensor signals for predicting an observed blood glucose may be found in Terence C. Mills, *Time Series Techniques for Economists*, Cambridge University Press, 1990, Peter R. Winters, *Forecasting Sales by Exponentially Weighted Moving Averages*, Management Science 6 (3): 324-342 and Rob J. Hyndman, Anne B. Koehler, J. Keith Ord, Ralph D. Snyder, *Forecasting with Exponential Smoothing: The State Space Approach*, Springer Series in Statistics, 2008.

In other embodiments, a prediction of a patient's sensor blood glucose level may also be based, at least in part, on an observed blood glucose variability. As such, while a patient's observed sensor blood glucose level may be within the patient's target range and significantly separated by upper and lower glucose threshold levels defining the target range, the patient's observed sensor blood glucose level may begin fluctuating or destabilizing (e.g., cycling within the target range). This may lead to a prediction of an out of target event in a near-future timeframe. It has been observed under certain hospital conditions, for example, that a patient's glucose variability may increase twenty-four hours prior to a hypoglycemic event.

Variability of a patient's blood glucose may be characterized using any one of several techniques. It should be understood, however, that claimed subject matter is not limited to any particular technique for characterizing variability of a patient's blood glucose. One technique includes determining a daily mean and standard deviation of a blood glucose level as discussed in Krinsley J S, "Glycemic variability: A strong independent predictor of mortality in critically ill patients", Crit Care Med vol 36, no 11, p3008-3013, 2008. Another technique may involve a determination of whether an observed blood glucose level is above an upper threshold and below a lower threshold over a twenty-four hour period as discussed in Bagshaw S M, et al., "The impact of early hypoglycemia and blood glucose variability on outcome in critical illness", Crit Care Med vol 13, no 3, pR91, 2009. Another technique may involve a determination of a mean absolute glucose change per hour (e.g., the magnitude and number of glucose cycles per hour) as discussed in Hermanides J, et al., "Glucose variability is associated with intensive care unit mortality", Crit Care Med vol 38, no 3, p838-842, 2010. Techniques for characterizing blood glucose variability may be applied to either a continuously monitored sensor blood glucose level or metered blood glucose samples providing a sequence of discrete points for computation. Using a continuously monitored blood glucose level, blood glucose variability may be characterized, at least in part, by measuring of a magnitude of, and timing between, peaks in an observed sensor blood glucose level. A patient's blood glucose level may also be characterized, at least in part, by a spectral analysis (e.g., using a Fourier transformation) including, for example, evaluation frequency patterns of glycemic changes.

As shown in FIG. 13, metered blood glucose sample measurements are taken on hourly intervals Q1 until the fifth hour at metered blood glucose sample 130. Here, while the observed blood glucose level is above a target range, a currently observed sensor blood glucose level and its slope (e.g., apparent first derivative with respect to time) suggest a trend that the patient's blood glucose is imminently entering the target range (e.g., before the next scheduled blood glucose reference sample). Here, responsive to blood glucose reference sample 130, a controller may extend a scheduled time for a subsequent metered blood glucose sample from Q1 (one hour) to Q2 (two hours). Responsive to the first metered blood glucose sample measurement within the target range 132 taken at the seventh hour, a controller may give an attendant or operator an option to extend a time for a subsequent metered blood glucose sample measurement from Q2 (two hours) to Q2+Q1 (three hours). Operation shown in FIG. 14 is similar to that shown in FIG. 13 except that an operator or attendant is given an option to extend a scheduled time for a subsequent metered blood glucose sample 136 from Q2 to Q2+Q2 (four hours). Operation shown in FIG. 15 is similar to that in FIG. 14, except that an attendant or operator is given the option to extend a time to a subsequent metered blood glucose sample measurement from Q1 (one hour) to Q2+Q2 (four hours) responsive to sample measurement 138 at the fifth hour, before receipt of any metered blood glucose sample measurement within the target range.

In a particular implementation, operation as illustrated in 13 through 15, in response to receipt of a metered blood glucose sample measurement a controller may evaluate the following conditions in determining whether an attendant or operator is to be given an option to extend a time for obtaining a subsequent metered blood glucose sample measurement:

Metered blood glucose sample measurement value is close to a high end of a target range (e.g., within 50.0 mg/dl);

Insulin infusion rate (if any) is expected to remain constant;

Patient's blood glucose at a subsequent scheduled blood
glucose reference sample time is predicted to be within
the target range;

RI exceeds a predetermined threshold;

Characterization of patient's glucose variability is below
a threshold; and

Limited change in the patient's insulin sensitivity.

In one implementation, a patient's insulin sensitivity may
be characterized by an observed or expected change in the
patient's blood glucose level in response to a dose of insulin.
This may be computed following each insulin dose by
observing changes in blood glucose level following the
dose. Alternatively, a patient's insulin sensitivity may be
computed over a particular time period (e.g., four hours,
twelve hours, twenty-four hours). Here, it may be observed
that an insulin sensitivity of a critically ill patient may
change rapidly as a disease state and metabolism fluctuate
and as different mediations may alter insulin sensitivity. In
one implementation, attendant or operator is to be given an
option to extend a time for obtaining a subsequent metered
blood glucose sample measurement at least in part in
response to application of a threshold computed insulin
sensitivity.

Figure 16:
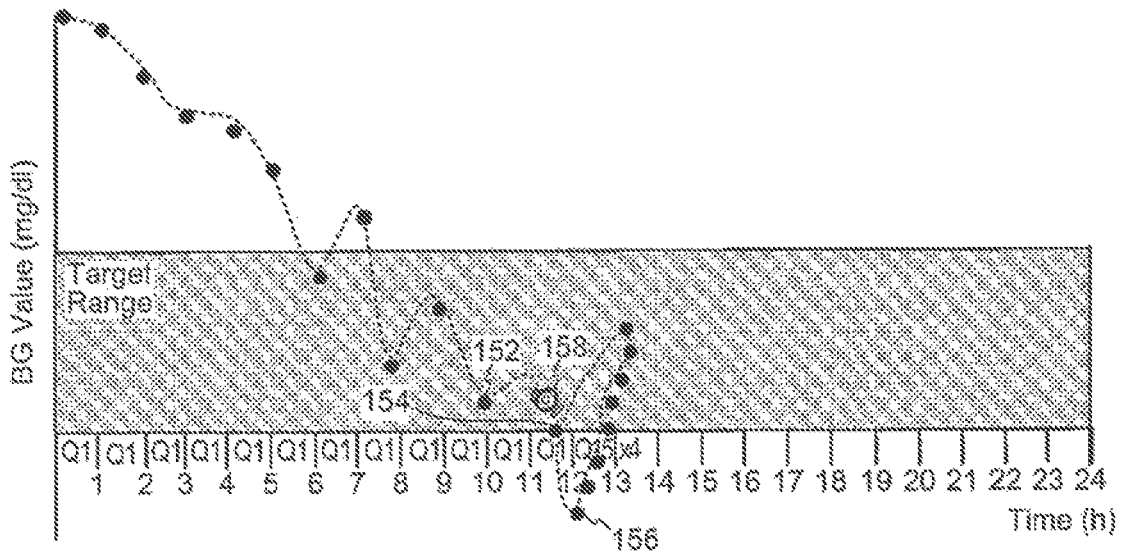
FIG. 16 is a plot illustrating adjustments to times between metered blood glucose sample measurements in response to a hypoglycemic event.

FIG. 16 illustrates an alternative implementation in which
a condition dictating more frequent metered blood glucose
sample measurements may be detected while the patient's
sensor blood glucose is still observed to be within a target
range. Here, between metered blood glucose sample mea-
surements 152 and 154, a continuous blood glucose moni-
toring system processing blood glucose sensor measure-
ments may observe a trend indicating that the patient's blood
glucose level may imminently transition outside of a target
range. As shown in the particular example of FIG. 16, at
point 158 between the eleventh and twelfth hours an event
may be triggered indicating a trend toward transitioning to
a hypoglycemic state. In one implementation, this event may
prompt or trigger corrective action such as, for example,
taking the patient off of insulin, starting intravenous dextrose
or both. In an alternative implementation, blood glucose
reference sample 156 in a hypoglycemic range may trigger
a state in which intervals between successive metered blood
glucose sample measurements are shortened (e.g., to 15
minutes as shown in FIG. 16 by the characters "Q15×4"))
until the blood glucose level returns to be safely within the
target range.

As discussed above, one factor in determining whether to
optionally extend a time for a subsequent metered blood
glucose sample includes a delay or lag between an actual
blood glucose level and a sensor blood glucose measure-
ment. Ideally, a blood glucose sensor and associated com-
ponent(s) would be capable of providing a real time, noise-
free measurement of a parameter, such as a blood glucose
measurement, that a control system is intended to control.
However, in real-world implementations, there are typically
physiological, chemical, electrical, algorithmic, and/or other
sources of time delays that may contribute to a sensor
measurement to lagging behind an actual present value.
Also, as noted herein, such a delay may arise from, for
instance, a particular level of noise filtering that is applied to
a sensor signal.

Figure 6:
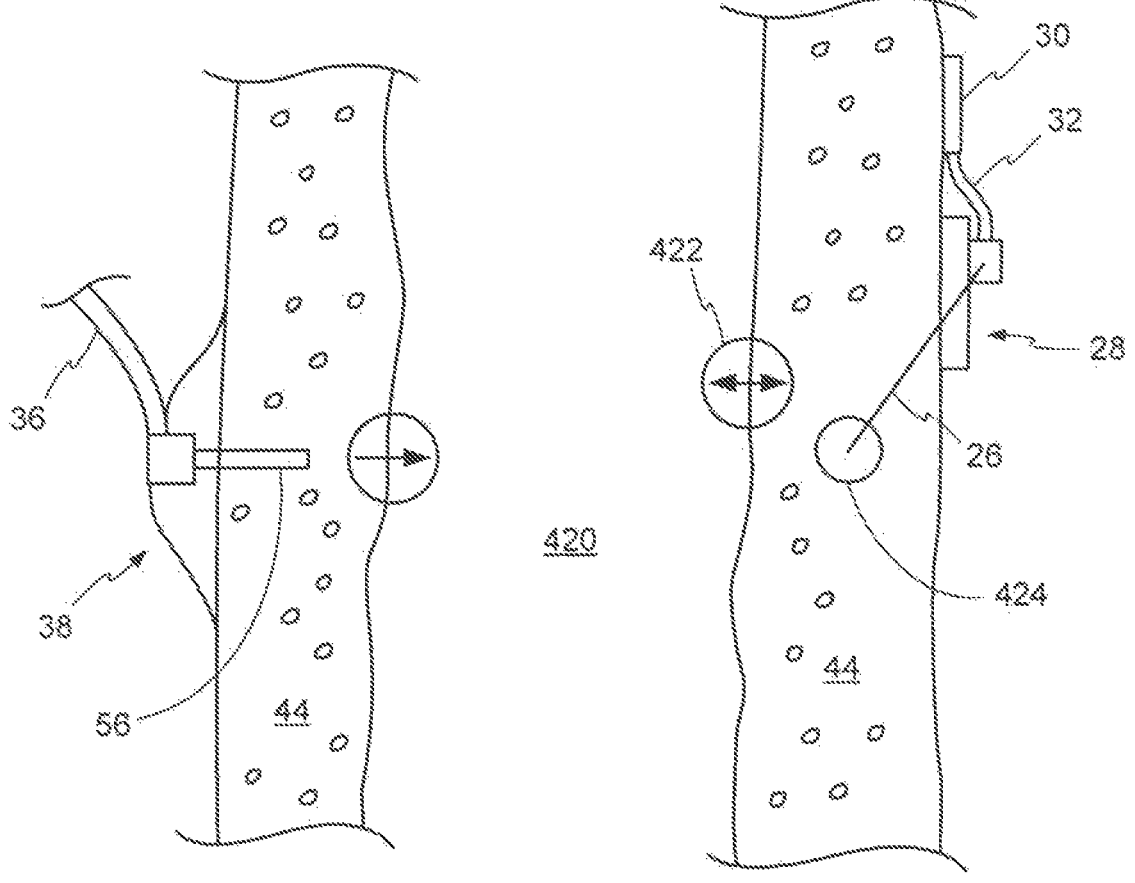
FIG. 6 is a cross-sectional view of an example sensor set and an example infusion set attached to a body in accordance with an embodiment.

FIG. 6 is a cross-sectional view of an example sensor set
and an example infusion set that is attached to a body in
accordance with an embodiment. In particular example
implementations, as shown in FIG. 6, a physiological delay
may arise from a time that transpires while glucose moves
between blood plasma 420 and interstitial fluid (ISF). This
example delay may be represented by a circled doubleheaded arrow 422. As discussed above with reference to
FIG. 1-3, a sensor may be inserted into subcutaneous tissue
44 of body 20 such that electrode(s) 42 (e.g., of FIGS. 3 and
4) near a tip of sensor 40 are in contact with ISF. However,
a parameter to be measured may include a concentration of
glucose in blood.

Glucose may be carried throughout a body in blood
plasma 420. Through a process of diffusion, glucose may
move from blood plasma 420 into ISF of subcutaneous
tissue 44 and vice versa. As blood glucose level changes, so
may a glucose level of ISF. However, a glucose level of ISF
may lag behind blood glucose level 18 due, at least in part,
on a duration for a body to achieve glucose concentration
equilibrium between blood plasma 420 and ISF. Some
studies have shown that glucose lag times between blood
plasma and ISF may vary between, e.g., 0.0 to 30.0 minutes.
Some parameters that may affect such a glucose lag time
between blood plasma and ISF are an individual's metabo-
lism, a current blood glucose level, whether a glucose level
is rising or falling, combinations thereof, and so forth, just
to name a few examples.

A chemical reaction delay 424 may be introduced by
sensor response times, as represented by a circle 424 that
surrounds a tip of sensor 26 in FIG. 6. Sensor electrodes may
be coated with protective membranes that keep electrodes
wetted with ISF, attenuate the glucose concentration, and
reduce glucose concentration fluctuations on an electrode
surface. As glucose levels change, such protective mem-
branes may slow the rate of glucose exchange between ISF
and an electrode surface. In addition, there may be chemical
reaction delay(s) due to a reaction time for glucose to react
with glucose oxidase GOX to generate hydrogen peroxide
and a reaction time for a secondary reaction, such as a
reduction of hydrogen peroxide to water, oxygen, and free
electrons.

Thus, an insulin delivery delay may be caused by a
diffusion delay, which may be a time for insulin that has
been infused into a tissue to diffuse into the blood stream.
Other contributors to insulin delivery delay may include, but
are not limited to: a time for a delivery system to deliver
insulin to a body after receiving a command to infuse
insulin; a time for insulin to spread throughout a circulatory
system once it has entered the blood stream; and/or by other
mechanical, electrical/electronic, or physiological causes
alone or in combination, just to name a few examples. In
addition, a body clears insulin even while an insulin dose is
being delivered from an insulin delivery system into the
body. Because insulin is continuously cleared from blood
plasma by a body, an insulin dose that is delivered to blood
plasma too slowly or is delayed is at least partially, and
possibly significantly, cleared before the entire insulin dose
fully reaches blood plasma. Therefore, an insulin concen-
tration profile in blood plasma may never achieve a given
peak (nor follow a given profile) that it may have achieved
if there were no delay.

Moreover, there may also be a processing delay as raw
analog sensor signals are processed for obtaining continuous
measurements of a patient's blood glucose concentration.
Description of such a processing delay contributing to a lag
between a present blood glucose concentration and a blood
glucose sensor measurement for example may be found in
U.S. patent application Ser. No. 12/347,716, titled "Method
and/or System for Sensor Artifact Filtering," filed on Dec.
31, 2008, and assigned to the assignee of claimed subject
matter.

Unless specifically stated otherwise, as is apparent from
the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:
determining a first glucose reference sample measurement for a patient according to a schedule;
determining timing information for obtaining a second glucose reference sample measurement based at least in part on a comparison of readings from a continuous glucose sensor to a first threshold and a difference between the first glucose reference sample measurement and an upper bound of a target range glucose level being less than a second threshold, wherein the first glucose reference sample has a value greater than the upper bound, wherein determining the timing information comprises determining a change to the schedule for obtaining glucose reference sample measurements for the patient; and
presenting an alert indicating the change to the schedule.

2. The method of claim 1, wherein the first glucose reference sample measurement and the second glucose reference sample measurement are metered glucose sample measurements.

3. The method of claim 1, wherein determining the timing information is based on a reliability of the continuous glucose sensor.

4. The method of claim 1, wherein determining the timing information comprises determining an earlier than scheduled time for obtaining the second glucose reference sample measurement.

5. The method of claim 1, further comprising causing at least one of: displaying a time the second glucose reference sample measurement is to be obtained, or causing an alarm to be presented.

6. The method of claim 1, wherein the comparison comprises comparing a glucose level of the patient and a predetermined target range, and wherein the timing information for obtaining the second glucose reference sample measurement is based on the comparison.

7. The method of claim 6, further comprising determining a duration of time the glucose level of the patient has been within the predetermined target range to determine the timing information.

8. The method of claim 6, wherein the predetermined target range is defined based on a target glucose level that varies over time.

9. The method of claim 6, wherein the glucose level is one of: an observed glucose level based on the first glucose reference sample measurement, or a predicted glucose level of the patient.

10. The method of claim 1, wherein determining the timing information for obtaining the second glucose reference sample measurement comprises determining a duration of time to delay obtaining the second glucose reference sample measurement from a scheduled time.

11. The method of claim 1, wherein determining the timing information comprises determining a trend of glucose levels of the patient based on the readings from the continuous glucose sensor.

12. The method of claim 1, wherein determining the timing information comprises determining a variability of glucose levels of the patient over a previous time period based on the readings from the continuous glucose sensor.

13. A system comprising:

one or more processors; and one or more non-transitory processor-readable media storing instructions which, when executed by one or more processors, cause performance of:

determining a first glucose reference sample measurement for a patient according to a schedule;

determining timing information for obtaining a second glucose reference sample measurement based at least in part on a comparison of readings from a continuous glucose sensor to a first threshold and a difference between the first glucose reference sample measurement and an upper bound of a target range glucose level being less than a second threshold, wherein the first glucose reference sample has a value greater than the upper bound, wherein determining the timing information comprises determining a change to the schedule for obtaining glucose reference sample measurements for the patient; and presenting an alert indicating the change to the schedule.

14. The system of claim 13, wherein the first glucose reference sample measurement and the second glucose reference sample measurement are metered glucose sample measurements.

15. The system of claim 13, wherein determining the timing information is based on a reliability of the continuous glucose sensor.

16. The system of claim 13, wherein the one or more processors further cause performance of determining an earlier than scheduled time for obtaining the second glucose reference sample measurement.

17. The system of claim 13, wherein the one or more processors further cause performance of at least one of: displaying a time the second glucose reference sample measurement is to be obtained, or presenting an alarm.

18. A method comprising:

obtaining a first glucose reference sample measurement for a patient according to a schedule;

determining timing information for obtaining a subsequent glucose reference sample measurement after the first glucose reference sample measurement to be used to calibrate a continuous glucose sensor based at least in part on a reliability of readings from the continuous glucose sensor and based on a comparison of readings from a continuous glucose sensor to a first threshold and further based on a difference between the first glucose reference sample measurement and an upper bound of a target range glucose level being less than a second threshold, wherein the first glucose reference sample has a value greater than the upper bound, wherein determining the timing information comprises determining a change to the schedule for obtaining a second glucose reference sample measurement for the patient; and presenting an alert indicating the change to the schedule.

19. The method of claim 18, wherein determining the timing information comprises determining an earlier than scheduled time for obtaining the second glucose reference sample measurement.

20. The method of claim 18, further comprising causing at least one of: displaying a time the second glucose reference sample measurement is to be obtained, or causing an alarm to be presented.

* * * * *